United States Patent
Marais (10) Patent No.: US 6,878,287 B1
(45) Date of Patent: Apr. 12, 2005

(54) DENTAL EQUIPMENT AND METHOD OF OPERATING SUCH EQUIPMENT

(75) Inventor: Jacobus Theodo Marais, Pretoria (ZA)

(73) Assignee: Radical Waters IP (Pty) Limited, Midrand (ZA)

( * ) Notice: Subject to any disclaimer, the term of this patent is extended or adjusted under 35 U.S.C. 154(b) by 0 days.

(21) Appl. No.: 10/182,899

(22) PCT Filed: Feb. 5, 2001

(86) PCT No.: PCT/ZA01/00009

§ 371 (c)(1),
(2), (4) Date: Oct. 21, 2002

(87) PCT Pub. No.: WO01/56616

PCT Pub. Date: Aug. 9, 2001

(30) Foreign Application Priority Data

Feb. 4, 2000 (ZA) .............................. 99/5028

(51) Int. Cl.$^7$ .............................. A61L 2/03; C02F 1/461
(52) U.S. Cl. .................... 210/748; 210/764; 210/198.1; 204/554; 204/660; 422/28; 433/80
(58) Field of Search ................................ 210/748, 764, 210/198.1, 205, 243; 204/554, 260, 660; 205/742; 422/28, 186.04; 134/166 C; 433/80, 88

(56) References Cited

U.S. PATENT DOCUMENTS

| | | | |
|---|---|---|---|
| 5,427,667 A | | 6/1995 | Bakhir et al. |
| 5,635,040 A | | 6/1997 | Bakhir et al. |
| 5,935,431 A | * | 8/1999 | Korin ........................ 210/205 |
| 5,947,727 A | | 9/1999 | Kimura et al. |
| 6,007,686 A | | 12/1999 | Welch et al. |
| 6,544,427 B1 | * | 4/2003 | Layton ....................... 210/764 |
| 2003/0052064 A1 | * | 3/2003 | Korin ........................ 210/760 |

FOREIGN PATENT DOCUMENTS

| | | | |
|---|---|---|---|
| DE | 28 36 532 A | | 2/1980 |
| JP | 07-299082 A | * | 11/1995 |
| WO | 99 20286 A | | 4/1999 |
| WO | 99 28238 A | | 6/1999 |
| WO | 00 24431 A | | 5/2000 |
| WO | 00 33757 A | | 6/2000 |

* cited by examiner

*Primary Examiner*—Frank M. Lawrence
(74) *Attorney, Agent, or Firm*—Nixon & Vanderhye P.C.

(57) ABSTRACT

An electrolytically activated, microcidal aqueous solution is disclosed which is used in the elimination and control of biofilm in dental unit water lines. The solution has a pH between 6.75 and 10 with microcidal as well as anti-oxidising, dispersing and surfactant properties, rendering the solution bio-compatible and non-corrosive, as well as capable of eliminating biofilm in dental unit water lines, while simultaneously dispersing and dislodging the biofilm from the water lines so as reduce the micro-organisms in the dental water to a predetermined level. The aqueous solution is produced using an electrolytic device that allows the independent manipulation of specific individual properties of two separate product streams (a cation-rich stream and an anion-rich stream), the manipulation being performed by separate and independent recirculation through the same electrode chamber or counter-electrode chamber of the electrolytic device to modulate the respective properties of the anion-containing and the cation-containing solutions.

20 Claims, 3 Drawing Sheets

Figure 1. Biofilm removal using anolyte

Figure 2 Regrowth of biofilm after treatment with anolyte and biofilm removal after treatment with the anolyte/catholyte (A-C) combination Figure 3. Biofilm before treatment Figure 4. Biofilm after 1h of biocide treatment Figure 5. Biofilm after 2h of biocide treatment Figure 6. Biofilm after 3h of biocide treatment Figure 7. Biofilm after 4h of biocide treatment Figure 8. Biofilm after 24h of biocide treatment

DENTAL EQUIPMENT AND METHOD OF OPERATING SUCH EQUIPMENT

This application is the U.S. national phase of International Application No. PCT/ZA01/00009, filed Feb. 5, 2001.

1. FIELD OF THE INVENTION

This invention relates to a dental operating unit for use in dental care, including procedures such as tooth cavity preparation, ultrasonic tooth de-scaling and root canal treatment; the use of a microcidal solution, with antioxidant as well as dispersing, surfactant and anabolic properties, that is suitable as a microcide as well as a cooling, lubricating and irrigating medium in dental care; an aqueous solution for use in the treatment of biofilm as well as a cooling, lubricating and irrigating medium in dental care; a method of treating biofilm, using such aqueous solution; dispensing means for dispensing such solution and a method of dental care, using such dental units and aqueous solutions.

2. BACKGROUND OF THE INVENTION

2.1. Dental Operating Units

Municipal, distilled or sterile water is commonly used in dental operating units (hereinafter respectively referred to as "dental units" or "DU's" and "dental unit water" or "DUW"). However, there is, considerable concern, internationally, over the possible contamination of the water lines in DU's. The concern is largely due to the biofilm that develops and is present in the tubing that leads into the DU's, is inside the units, and leads from the units to the handpieces.

Biofilm often harbours potential pathogens. It is well established that microbes such as *Pseudomonas, Mycobacterium* and *Legionella* have already been isolated from dental unit water lines (herein referred to as "DUWL's").

The potential and the implications of pathogens being iatrogenically transmitted to patients undergoing dental treatment are obvious, Including the risk of disease and even death. It would appear that the use of municipal water directly connected to DU's could be considered substandard level of care. In many third world countries, municipal water is not always effectively disinfected.

To overcome the problem and thus minimise the risk, the use of independent water systems, sterile water systems and/or microfilters have been suggested. The independent water systems or sterile water systems (herein referred to as "IWS's" and "SWS's" respectively) consist of a container, pressurised by compressed air delivered from a standard dental compressor. It was also advised that a strict maintenance regime, consisting of daily flushing and purging with sodium hypochlorite be followed. A few of the disadvantages of the suggested regime are the time, effort and the discipline required for daily change of filters, the corrosive action and toxicity of sodium hypochlorite, the possibility of contamination of the sterile water by unclean compressed air, the current cost of procuring sterile water and the formation of biofilm. In fact, due to the absence of any residual disinfectants, SWS's experience an even greater build-up of biofilm than systems connected to municipal supplies.

2.2. Biofilm 2.2.1 Introduction

Adhesion to surfaces is a common and well-known behaviour of micro-organisms in oligotrophic habitats. This adhesion and the subsequent microbial growth lead to the formation of biofilms. Bacterial biofilms promote increased biomass deposition, resulting in resistance to fluid flow, microbial induced corrosion and, in industrial water cooling systems, loss of heat exchange capacity.

Industries control unwanted biofilms, with varying degrees of success, by using biocides. The use of biocides, especially chlorine, in water reticulation and heat exchange systems is however effective only if the biofilm is removed mechanically or physically. Chlorination of a mature biofilm is often unsuccessful because the biocide only reacts with the outer layers of the biofilm, leaving a healthy and substantial bacterial community on the surface of the substrate that rapidly regrows. Bacteria within biofilms also develop increasing resistance to biocides on repeated dosing. It has been found that biocides further induce crossresistance to other biocides.

Microbial biofilms are problematic in a range of industrial environments, where large areas of submerged surfaces are exposed to relatively high nutrient fluxes, providing niches for the formation of copious surface-associated growth. Bacterial colonisation of surfaces in an aqueous environment is a basic stratagem for survival in nature as nutrients are more available at the solid—liquid interface. The resulting aggregates form microcolonies, which develop into biofilms.

A range of bactericidal substances, commonly termed biocides or microbicides, are available, all of which are claimed by their producers quantitatively to kill bacteria occurring in aqueous systems. Biocides target a range of cellular loci, from the cytoplasmic membrane to respiratory functions, enzymes and the genetic material. However, different bacteria react differently to bactericides, either due to inherent differences such as unique cell envelope composition and non-susceptible proteins, or to the development of resistance, either by adaptation or by genetic exchange. Bactericides should therefore be evaluated against the organisms, which they are chosen to control, i.e. the dominant ones in the system to be treated. The composition of microbial populations in systems varies with the type of water used, and changes considerably after treatment with various biocides by selection for resistant strains. Bacteria growing as biofilms are also significantly more resistant to most of the currently known antimicrobial agents, posing ongoing challenges for methods for their control.

2.2.2. The Adhesion of Biofilm in Dental Operation Units

Biofilm comprises a combination of an active layer of sessile, i.e. attached/adherent, micro-organisms, which can include bacteria, and an inert glyco-calyx matrix (hereinafter referred to as "GCM"). The biofilm attaches to any surface in contact with fluids, including conduits used for the conveyance of fluids. While biofilm can grow in any solution, including aviation fuel, the solutions for purposes of this discussion will be limited to aqueous solutions in DUWL's.

Biofilm contamination is a dynamic process due to many factors, including:
long periods of stagnation,
  high surface to volume ratio,
nutritional content of water for microbial survival,
mineral content and hardness of water facilitating coating of
  the lumen,
fluid dynamics,
low flow rate, and
microbial quality of the water entering the system.

Biofilm is routinely found in DU's. Biofilm is formed when planktonic bacteria adhere to the inner luminal walls of the DUWL's and/or within the dental unit water delivery systems (hereinafter referred to as "DUWDS's"). In an aquatic environment, such as the DUWL's, molecules with hydrophobic or other functional groups can adsorb to the inner surfaces of the DUWL's to form conditioning films. Planktonic bacteria from the water adhere to these conditioning films, laying the basis for a biofilm matrix.

Some bacteria can immediately form a firm passive attachment to surfaces. Other bacteria become attached in a more active adhesion process through secretion of exopolysaccharide glyco-calyx polymers, the latter serving to anchor the biofilm to the surfaces. Micro-organisms, when coming into contact with a substrate such as the inner surface of the DUWL's, activate mechanisms through which they preferentially adhere to that surface. These so-called adherence mechanisms are mediated, by amongst others, electrostatic attraction and hydrogen bonding. Additionally, substantial metabolic changes occur in the micro-organisms upon adherence to the substrate, with the sessile micro organisms generating specific metabolic bi-products. These bi-products serve as the building blocks of the GCM that constitutes the inert component of the biofilm.

While most disinfectant chemicals, when applied at the recommended dosages, serve to control both the planktonic and sessile micro-organisms in the water and on the inner surface of the DUWL's, few, if any, possess the capacity firstly to control or eliminate the micro-organism population in the biofilm, and secondly to cause a permanent elimination of the inert GCM adherent to the DUWL's.

At the inner surface of the DUWL's, and specifically at the interface between those areas of the inner surface covered by the GCM and the exposed surfaces, biochemical oxidation-reduction reactions influence the continued adherence of the GCM to the DUWL's. The exposed inner surfaces of the DUWL's act as a positively charged anode, while the GCM covered surfaces act as a negatively charged cathode for purpose of these reactions. The establishment and maintenance of the potential difference across the interface between the GCM covered and exposed inner surfaces of the DUWL's ensures the continued growth and stability of the viable biofilm, thus holding the key to the disruption of the particular adherence mechanisms.

Conventional chemical disinfectant compounds are unable to influence the micro-biochemical redox reactions and as a result fail to dislodge and/or eliminate the GCM in disinfectant treated biofilms.

Dispersing products with specific surfactant properties have been employed, with limited success, to dislodge the GCM, but these products either do not have microcidal properties or are incompatible with known microcidal chemicals.

Biofilm growth has been observed inside plastic DUWL's in as little as two weeks. Biofilm, when viewed through a Scanning Electron Microscope (hereinafter referred to as "SEM"), is found to be characterised by micro-organisms embedded in a matrix. This matrix, ranging from 30 to 50 microns in thickness, could allow fragments of material/ biofilm to dislodge, thereby contaminating other areas of the DUWDS's.

2.2.3. Pathogenicity of Micro-organisms in Dental Unit Water Lines

The colonisatlon and the proliferation of many and varied species of micro-organisms in DUW and DUWL's are well documented. Although many micro-organisms found in this environment can be pathogenic potentially, three genera in particular are of concern for the dental office, namely *Pseudomonas, Mycobacterium* and *Legionella*. *Pseudomonas cepacia*, i.e. a Gram negative bacillus, has been spread to patients in hospital settings through its presence in aqueous disinfectants. This species is very resistant to chemical agents and the colonisation by this species of bacteria has been demonstrated when reservoirs of chlorhexidine gluconate have been "topped-up" without cleaning the reservoirs first. Several species of *Mycobacterium* have been isolated from hospital water supplies, some of which have been associated with hospital related infections. In one case, *M. xenopi* was implicated in 19 cases of pulmonary disease in a Veterans Administration hospital. The transmission occurred through infectious aerosols when patients used a shower. Water spray aerosols are commonplace in the dental setting, such as in the high-speed handpiece operation and the air-water syringe rinsing with high-speed evacuation. Aerosols generated by the water-cooling component of dental handpieces were found to be the source of sub-clinical infection with *Legionella pneumophila* in a dental school environment. It was found that of 270 sera tested 20% had significantly higher IgG antibody activity to the pooled *Legionella* sp. antigen as compared with known negative controls. Also, a high prevalence of antibodies to *Legionella pneumophila* among dental personnel was found. Studies demonstrated the highest prevalence (50%) among dentists who were constantly exposed directly to the aerosols generated when high-speed drills and sprays were used. Another study found that 68% of DUW samples collected from 28 dental facilities in six U.S. states showed the presence of *Legionella* spp. This study also showed that 61% of water samples of comparative potable water from domestic, institutional faucets and drinking water fountains also contained *Legionella* spp, and that there was no significant difference between the two.

2.2.4. Corrosion Caused by Biofilm

Biofilm promotes corrosion of metals by creating differences in potential electrical charge across surfaces and by harbouring sulphur-reducing bacteria. Also, they increase frictional resistance and loss in fluid flow, and by acting as an insulating layer, decrease the rate of heat transfer. The corrosion phenomena are collectively termed microbially induced corrosion (hereinafter referred to as "MIC"). As the costs attributable to MIC are high, effective control of bacterial numbers in industrial aqueous environments is essential. Microbially induced corrosion is caused by the presence of bacteria in water systems, especially by bacterial biofilm.

2.3. Removal of Biofilm

The American Dental Association (ADA) stated, in 1996, that by the year 2000, all DUW should contain less than 200 colony-forming units (CFU) (bacteria and other colony forming microorganisms) per millilitre. At present, it is known that DUW in most dental operatories contain in excess of half a million CFU/ml. The more sophisticated the testing techniques, the more bacteria are found in DUW.

It is thus imperative that bacterial biofilm must be removed from DUWL's. The following are some of the most common methods for biofilm removal currently being followed, namely:

bacteria are chemically killed by application of lethal doses of bactericidal compounds or so-called biocides, biofilm is released and/or dispersed by surfactants and/or dispersants, biofilm is physically removed by a variety of processes, biofilm structures are weakened by enzymes or chelants of divalent cations, biofilm is physically removed by applying an alternating current or ultrasonic sound waves across the biofilm, and planktonic bacterial numbers are controlled by the use of ultraviolet light.

2.3.1. Physical Methods of Removal of Biofilm

Several methods have been suggested by which the contamination of DUWL's might be minimised or avoided physically. Many DU's today are equipped with anti-retraction valves to prevent suck-back and/or are designed to give a short 'terminal flush' of water through hand pieces after operation. Flushing of DUWL's at the beginning and end of patent treatment has been advocated previously. The suggested flushing protocol, as recommended by the U.S. Department of Health and Human Services, could diminish planktonic organisms, but will not eliminate or control biofilm. One study concluded that a two-minute flushing reduced the counts of planktonic organisms, on average by one-third, but did not reduce counts to zero. Many researchers have suggested flushing water lines with various disinfectant solutions, which include hydrogen peroxide, chlorhexidine gluconate, sodium hypochlorite, povidoneiodine and mouthwash. None of these methods however has been shown to eliminate biofilm or prevent its formation.

The microbial quality and mineral content of tap water varies depending upon the source, processing, distance from the processing plant and storage reservoirs, and seasonal variations. The ADA's statement on dental unit waterlines implies that there must be a control over the quality of water to be used in events such as "boil water alerts" in the community. This cannot be achieved merely by cleaning or disinfecting the DUWL's periodically. One way to prevent contamination from municipal sources would be to retrofit the DUWS's with a self-contained reservoir and detach the DUWS's from the municipal water source. There are many self-contained water systems with a range of volumetric capacity, function and cost. However, very soon after such an installation, an "independent", new, biofilm which feeds on itself can and does form, leading to similar kind of contamination. Indeed, the mere act of installing the self-contained water system will not eliminate any existing biofilm.

Tap water can be treated in a variety of ways to meet the ADA's goal. Boiling, pasteurisation, filtration, distillation, sterilisation and utilisation of chemical additives (approved germicides) are some of the methods that may be efficacious In controlling the level of contamination in tap water. Some filters (eg. activated carbon casing fused to a high intensity UV light) have been used to improve source water. Commercially available distilled and bottled water is not microbiologically reliable for dental use. In any event, the real source of contamination is not the water introduced into the system, but rather the self-perpetuating "resident" biofilm. If sterile water is fed into a system with a well-developed biofilm, the water that is delivered at the end will be heavily contaminated.

There are many physical and chemical methods of improving dental treatment water quality. Today, membrane filters antimicrobial impregnated filters/cartridges and membrane filters that have the capability of controlling water microbes and endotoxins are being marketed for use in DUWL's. Most available membrane filters are consistent in controlling microbes/planktonic micro-organisms in dental treatment water, while membrane filters with the additional function of endotoxin retention are even more beneficial. It is essential to change the filters according to the manufacturers' recommended optimal performance time. For the filters to be effective, they must be installed in close proximity of the outlets (handpieces and syringes), because of the possibility of biofilm in the tubing at or towards the outlets of the DUWL's. This proximity represents an untenable situation, because the filters are bulky and thus impact negatively upon the ergonomic handling characteristics of the dental handpiece or the triplex syringe.

2.3.2. Chemical Treatment of Biofilm in DUWL's

Chemical treatment to control the microbes and biofilm in DUWL's are some of the options available to dentists. Two issues are at stake, namely safety and efficacy. The chemicals must kill all microorganisms, not only in the water but also in the biofilm. The chemicals must also dissolve, disperse and remove the biofilm. The chemicals selected must be approved by the FDA for use in the jurisdiction of the United States, safe for patients, inert to teeth and other human tissue in and around the mouth and non-corrosive to the components of the DUWS's and compatible with other materials used In the patient's mouth. One such example is a low concentration of citric acid in the DUWS's. Other examples are chlorine dioxide, chlorhexidine and iodine. These chemicals are contra-indicated in patients with suspected allergies, hypersensitivity's, and possible contraindications when used with certain aesthetic restorative materials. The use of bactericides to control biofouling in water cooling systems is an accepted practice. It is essential to apply the correct dosage at the correct frequency. Incorrect use of biocide gives poor results and is expensive. The building blocks of a successful biocide programme are ideally considered to be the knowledge of the organisms to be killed; the selection of the correct biocide or combinations and their respective concentrations; a scientific determination of dosage frequency; monitoring the control of micro-organisms through analysis and data processing; and monitoring microbial attachment to surfaces.

Water treatment bactericides fall into two categories, oxidising bactericides (e.g. chlorine and hydrogen peroxide) and non-oxidising bactericides, which can be divided into five groups, based on their chemical nature or mode of action.

Oxidising biocides are general chemical oxidants. They are not selective for living organisms, but react with any oxidisable matter. However, they are bactericidal because certain bacterial cell components can react readily with them, having a higher reduction potential than most other chemicals present in water. Three classes of oxidising biocides are available for bactericidal applications; oxidising halogens, peroxides and ozone. Peroxides are unstable oxygen compounds that decompose to form free hydroxyl radicals, which in turn react oxidatively with organic compounds. The peroxides include hydrogen peroxide, peracetic acid, aromatic peroxyacids, persulphates and calcium peroxide.

Hydrogen peroxide is an ideal water treatment bactericide as it is stable if stored correctly, non-corrosive and it is totally miscible with water. It has good antimicrobial properties and decomposes to water and oxygen, leaving no toxic waste. Hydrogen peroxide however penetrates cells, causing site-directed damage due to metal-dependant OH formation. It causes DNA strand breaks and base hydroxylation. Guanine and thymine are the two main targets of peroxide-generated free radical attack. The resulting 7,8-dihydro-8-oxoguanine mispairs with adenine whereas thymine oxidation products stop DNA polymerase, halting replication. Most bacterial mutants cannot survive due to incoherent metabolism, so that peroxide treatment at low concentration leads to slow death. Hydrogen peroxide also inhibits mitochondrial ADP-phosphorylation.

The development of resistance to oxidising bactericides has not been reported in the biofouling control literature.

However, a variety of bacteria, mostly fermentative, exhibit oxidising stress response by producing oxidant degrading and repair enzymes. These include *Escherichia coli, Salmonella typhimurium, Bacillus subtilis* and *Pseudomonas fluorescens*. Stress response means that cells become more resistant to a deleterious factor within hours of exposure to sub-inhibitory quantities of the factor. A variety of defense genes have been characterised in *Escherichia coli*, encoding various superoxide dismutases, catalyses, alkyl hydroperoxide reductases and glutathione reductases, as well as DNA repair enzymes. In addition various regulatory genes have been characterised, including OxyR, Re~ and SoxR. These regulators determine intracellular redox potential, and activate stress response when cells are exposed to oxidising agents.

Peracetic acid is the best known of the organic peroxides. Like hydrogen peroxide, it forms free hydroxyl radicals, which react with various protein structures and DNA. In addition, the dissociation of peracetic acid leads to formation of acetic acid, which is mildly antibacterial itself. Application of peracetic acid to systems does not leave any toxic waste behind. Water hardness or organic contamination does not affect the antibacterial activity of peracetic acid.

Hypochlorous and hypobromous acids possess excellent antibacterial activity, although within a defined pH range. Hypochlorous acid is used in various applications to prevent, control, or decrease bacterial activity. Hypochlorite is used among others in industrial water systems to control biofouling. The antibacterial mechanism of action of hypochlorite is not clear to date although much work on the mechanism of action In eukaryotic cells has been done. HOCl does not enter freely into eukaryotic cells but attacks surface and plasma membrane proteins, impairing transport of solutes and the salt balance. It oxidises sulfhydral groups and inhibits plasma membrane ATPases. It appears to halt protein synthesis in cells at low concentrations for ca. 2 hours following exposure. However, it does not cause any damage to eukaryotic genomic material. The stability and antimicrobial activity of hypochlorous acid is dependent on pH. It dissociates at pH greater than 7 and the undissociated moiety is the antibacterial one. Above pH 7,5 it looses its antibacterial activity. It is excellent for biofouling control as it weakens the extracellular polysaccharide (EPS) structure, leading to sloughing and removal of sections of the biofilm.

Ozone is a strong oxidising material capable of killing bacteria and algae and of inactivating viruses. It is an unstable gas. It further degrades the EPS holding biofilms together, so that treatment results in loosening of the biofilm. This leads to loosening of scale from the surface. Ozone has a very short half-life and therefore has to be generated on site. In distilled water its half-life at 20° C. is 25 minutes. Its solubility in water is 13 times that of oxygen. Upon reaction with organic material, it decomposes to oxygen. It does, however, react with several cations and anions such as $Fe^{2+}$, $Mn^{2+}$, $MnO_4$, $NO^{2-}$, and CN. Ozone is toxic to humans, and detectors should be installed together with ozone generators. However, treated water is perfectly safe as ozone degenerates to oxygen.

Sodium hypochlorite (NaOCl) is universally used for root canal irrigation, its principal functions in root canal treatment being microcidal, dissolving organic material and lubrication. NaOCl is also very effective in biofilm control and improving dental treatment water quality, but there are substantial disadvantages, such as that it is highly toxic and even fatal in concentrated form, particularly at the concentrations at which it is at its most effective as an irrigating medium. Further, NaOCl is also very corrosive and is therefore damaging to the DUW system in the medium to long term. Recent studies have shown sodium hypochlorite to be corrosive to teeth, causing tooth embritllement. High amounts of tri-halomethanes are produced when in contact with organic matter such as biofilm. Constantly present low concentrations of NaOCl in the presence of organic matter increase the total trihalomethane levels beyond levels set by the U.S. Environmental Protection Agency. It is therefore quite understandable that the U.S. FDA has refused to date to approve the use of NaOCl for the specified standards set.

Electrolytic activation ("EA") technology is based upon the generation, by means of specialised electrolytic systems, of metastable activated solutions. These solutions are the derivatives of basic water molecules that display abnormal physico-chemical and catalytic activity. The source components of these activated water solutions are simply potable water and a small quantity (typically 0.1–10 g/l) of salt. During Electrolytic Activation (herinafter referred to as "EA") of water, a diluted saline solution is "activated" by passing it through electrolytic cells of any one of a multitude of designs.

2.4. Electrolytic Activation 2.4.1. Electrolytically Activated Water and Treatment of Biofilm The author, in accordance with the requirements of this invention, utilised a cylindrical electrolytic device, having at least one electrolytic cell, in which the anodic and cathodic chambers are separated by a permeable membrane and the specific design of which permits the harnessing of two distinct, separate and electrically opposite product streams of activated water.

During the period of increased activity, these meta-stable solutions have been shown to have applications in a diverse array of technological processes, often as a substitute for traditional chemical agents. Irrespective of the characteristics of the specific solution, where activation status can extend from hours to days, the resultant meta-stable solutions following decay of the state of activation revert to benign water or dilute saline.

The ability to consistently produce a solution of a specific quality, possessed of unique and proven attributes, on a demand driven basis, with no adverse environmental or toxic consequences, significantly differentiates electrolytic activation technology from current customary technologies in biofilm treatment.

In addition, the ability to consistently produce two distinct, separate and electrically opposite product streams of activated water of specific quality as well as unique and proven attributes, on a demand driven basis, with no adverse environmental consequences, significantly differentiates the electrolytic device applied in this invention from the electrolytic devices previously utilised or proposed for utilisation in the dental industry.

2.4.2. Principles of EA Technology in a Cylindrical Electrolytic Device

Water of varying mineralisation is passed through the cylindrical electrolytic cell, the specific design of which permits the production of two distinct and electrically opposite streams electrolytically activated, low concentration saline solutions.

The design of the specific cylindrical cell utilised by the author for this invention is such as to ensure a uniformly high voltage electrical field through which each microvolume of water must pass. This unipolar electrolytic activation created by potential gradient of about a million volts per cm in a thin layer at the surface of the electrode results in the creation of solutions whose pH, oxidation reduction potential (ORP) and other physico-chemical properties, lie outside of the range which can be achieved by conventional chemical or most electrolytic means.

Two separate streams of activated solutions are produced, namely anolyte and catholyte, with the anolyte typically having a pH range of 2 to 9 and an oxidation- reduction potential (ORP) of +150 mV to +1200 mV, depending on the production conditions. The anolyte is an oxidising agent due to a mixture of free radicals and has an antimicrobial effect. The catholyte that is produced typically has a pH of 8.5 to 13 and an ORP of about −150 mV to −900 mV, depending on the production conditions. The catholyte has reducing, dispersing and surfactant properties and is an antioxidant.

One of the advantages of the design of the specific cylindrical cell utilised by the author for this invention is that the chemical composition of the two solutions can be altered by utilising various hydraulic arrangements, linking electrolytic cell modules with other supplementary devices in order to optimally address the requirements of specific areas of application. Some other variables are the quality of the water used, flow rate; hydraulic pressure; current density; and voltage on the electrodes.

Aside from its distinctive attributes, as well as the possibility of mixing the two solutions, at least a fraction of the negatively charged anti-oxidant solution, i.e. the catholyte, can also be channelled back into the anode chamber, thereby modulating the quality of the positively charged oxidant solution, i.e. the anolyte, that is produced. Similarly, at least a fraction of the anolyte, can also be channelled back into the cathode chamber, thereby modulating the quality of the negatively charged antioxidant solution, i.e. the catholyte, that is produced. Depending on the specifications of the required application, variations in the design of the hydraulic systems can be effected to meet the requisite objectives.

The design of the specific cylindrical cell utilised by the author for this invention is therefore such as to ensure a uniformly high voltage electrical field through which each micro-volume of water must pass.

Therefore and when mixed together, post production and extrinsically to the generating device, in the "as produced" ratios, or when at least a portion of either the anolyte or the catholyte is recycled through the generating device for further activation, the anolyte and/or catholyte form a unique solution, with very specific characteristics, including microcidal and anti-oxidant as well as surfactant properties. For purposes of this specification, the term "mixed" therefore shall be interpreted so as to mean the adding of the anolyte and the catholyte together post production and extrinsically to the generating device, whilst "recycling", "activating" and/or "generating" shall be interpreted so as to mean the reactivation of the particular solution in the generating device, with cognate terms having corresponding meanings.

2.4.3. Properties of Electrolytically Activated Solutions

The properties of electrolytically activated solutions are dependent upon a number of factors. These factors comprise the solution flow rate through the cell, type of salt, the voltage and current being applied, temperature, inter-flow dynamics of the solutions between the anode and cathode chambers, such as the degree of mixing, recycling, with feedback of catholyte into the anolyte chamber and/or vice versa, the design and geometry of the cell and the degree of mineralisation of the water.

During the process of electrolytic activation in the electrolytic cell utilised by the author, three broad classes of product are believed to be produced:

Stable products—these are acids (in the anolyte) and bases (in the catholyte)—which influence the pH of the solution in question, as well as other active species.

Highly active unstable products—these include free radicals and other active ion species with a typical lifetime of less than 48 hours. Included here are electrically and chemically active micro bubbles of electrolytic gas of 0.2–0.5 micrometer in diameter and with concentrations up to $10^7$ $ml^{-1}$, distributed uniformly through the solution. All these species serve to enhance the ORP of the anolyte, which is oxidising.

Quasi-stable structures—these are structures formed at or near the electrode surface as a consequence of the very high voltage drop ($10^6$ V $cm^{-1}$) in those regions. These are free structural complexes of hydrated membranes around ions, molecules, radicals and atoms. The size of these water clusters is reduced to approximately 5–6 molecules per cluster. All these features enhance the diffusion, catalytic and biocatalytic properties of the water.

It is important to note that the level of mineralisation of input water required to generate optimally metastable solutions is insignificantly different from the composition of potable water. However, the heightened electrical activity and altered physico-chemical attributes of the solutions differ significantly from the inactivated state, but yet remain non-toxic to mammalian tissue and the environment. Without maintenance of the activated state, these diverse products degrade to the relaxed state of benign water and the anomalous attributes of the activated solutions such as altered conductivity and surface tension similarly revert to pre-activation status.

2.4.4. Biocidal Properties of Anolyte and Mixed/Recycled Anolyte and Catholyte.

Most of the earlier technologies that have employed electrolytic activation to generate biocidal solutions have not been capable of separating the anolyte and catholyte solutions during generation in the cell. In these earlier technologies, the two opposing solutions have greatly neutralised each other with regard to potential electrical activity.

One of the advantages of the more modem EA systems is that the biocidal activity of hypochlorous acid generated in these systems has been observed in tests to be up to 300 times more active than the sodium hypochlorite generated by earlier systems. Additionally, comparison of neutral anolyte (pH=7) with alkaline gluteraldehyde (pH=8.5) showed that the latter required a concentration of 2% versus 0.05% of the former, in order to achieve the same biocidal efficacy. Similarly, it has been shown that a 5% solution of sodium hypochlorite (Jik) can only be used for purposes of disinfection whilst a 0.1% to 0.03% solution of neutral anolyte, has both disinfectant and sterilising properties, under similar test conditions. In general, the biocidal activity of non-activated neutral Anolyte is 80 times the potential activity of the hypochlorite solution, but still exhibits one third of the full biocidal potential of the optimally activated ECA solution.

This heightened biocidal capacity relative to traditional chemical solutions permits the incorporation of activated solutions at substantially lower dose rates, thereby obviating the risk of toxicity and adverse environmental impact, whilst providing cost effective resolutions.

2.4.5 Acidic Anolyte Solutions in Dental Units

The use of electrolytically activated low concentration saline solutions as biocides in DUWL's is proposed and disclosed in numerous documents, including international patent application PCT/US99/29013, published under WO 00/33757. PCT/US99/29013 proposes the use of acidic electrolysed water having a pH of 2.5 to 6.5 in continuous contact with the interior surfaces of the DUWL's during operation of the dental appliances, both as biocide for the biofilm and as operating fluid for the dental appliances.

PCT/US99/29013 focuses on two types of electrolytic systems, both producing their acidic anolyte from a plate reactor-type, electrolytic cell, and proposes that it is incorporated into dental systems for disinfecting and reducing of bio-film in DUWL's. The first system makes use of a membrane to separate and generate distinct anolyte and catholyte solutions. This system generates very acidic anolyte at a pH of 2 to 3.5. The second system does not use a membrane and generates only one stream of solution. PCT/US99/29013 proposes the addition of HCl (hydrochloric acid) into the feed of the second system, so as to increase the concentration of chlorine ions and to lower the pH even further, thus improving the microcidal efficacy of the anolyte.

A material disadvantage of the acidic anolyte solutions proposed in PCT/US99/29013 is their toxicity, due to their relatively high chlorine and sodium hypochlorite content. In fact, it is believed that there is relatively little difference between the acid anolyte solutions as proposed and bleach, with the latter being substantially simpler and cheaper to procure.

A further disadvantage of the acidic anolyte solutions proposed in PCT/US99/29013 is that they are advocated merely to reduce bio-film, and thus their apparent inability to eliminate bio-film, potentially allowing the DUWL's to develop resistant strains of bio-film, with the accompanying implication of serious health risks. More particularly, PCT/US99/29013 only proposes the disinfection of the DUWL's with reference to the cited microbial results, but does not propose the sterilisation of the DUWL's nor does it disclose any evidence of the removal of biofilm from the inner surfaces of the DUWL's. In fact, it is common knowledge that disinfection of water does not show/prove elimination or even reduction in bio-film.

In addition, PCT/US99129013 makes reference to the use of Japanese electrolyzers, which, as reported in a scientific paper published by Horiba et al in Oral Surgery, Oral Medicine, Oral Pathology, Volume 87, No.1, January 1999, proved ineffective against *Bacillus subtilis*, thus demonstrating that the different electrolytic devices produce different solutions with varying levels of efficacy.

Further and with reference to the adding of a dilute HCl solution to the electrolyser to increase the chlorine concentration, resulting in additional chlorine ions which increases the microcidal effect, it is believed that the acidic solutions without the added HCl is sub-optimally effective. It has been well documented that HCl, although a very effective biocide, has proven sub-optimal efficacy against bio-film—thus by adding HCl to the process water, one may improve the microcidal efficacy of the product to some extent but not the removal of the biofilm. Furthermore, such a product would be more corrosive than one with a higher pH and a lower chlorine content.

In addition, the relatively high concentrations of sodium hypochlorite generated result in the generation of relatively high levels of tri-halomethanes, particularly at lower pH values, thus increasing the carcinogenic potential of the solutions. PCT/US99/29013 thus proposes the use and incorporation of a sodium hypochlorite generator, which has contingent disadvantages and which defeats the whole purpose of using electrolytically activated saline solutions as biocides.

3. OBJECT OF THE INVENTION

It is accordingly an object of this invention to provide dental equipment; a microcidal solution, having antioxidant, dispersing and surfactant properties, for the disinfection, elimination and effective control of bio-film in dental unit water lines and which is in addition suitable for use also as a cooling, lubricating and irrigating medium in the dental unit and associated dental appliances; and a method of treating biofilm in DU's, using such dental unit, solution and aqueous solution.

It is a further object of this invention to provide dental equipment, a microcidal solution, having antioxidant, dispersing and surfactant properties, and a method of treating biofilm in dental units that will
1. Eliminate biofilm in the waterlines effectively;
2. Reduce corrosion potential and corrosivity when compared to the various other types of anolyte solution;
3. Increase compatibility with mammalian tissue when compared to sodium hypochlorite (bleach, Jik) as well as the various other types of anolyte solution, and as a result, can be used continuously and in an "online" manner in the DUWL's and DUWS's in the presence of and on patients;
4. Obviate the need for separate or dedicated effluent disposal facilities in the absence of an effluent steam; and
5. Reduce the risk of halomethane formation such as that of trihalomethanes.

4. SUMMARY OF THE INVENTION

According to a first aspect of the invention there is provided dental equipment comprising a dental unit, having an arrangement of water lines; an electrolytic device, for producing an electrolytically activated, anion containing and cation containing aqueous solution for use in the treatment of biofilm in the dental unit water lines, the solution being characterised in having microcidal as well as dispersing and surfactant properties capable of eliminating fluid-born and sessile bio-organisms as well as dispersing inert glyco-calyx matrices (hereinafter referred to as "GCM"), thus assisting in the elimination of the biofilm in the water lines; and means for introducing the aqueous solution into the water lines for treating the biofilm.

The aqueous solution may consist of a mixture of an electrolytically activated, anion-containing solution and/or an electrolytically activated, cation-containing solution. The aqueous solution may consist of a mixture of the electrolytically activated, anion-containing solution and the electrolytically activated, cation-containing solution in the proportions and the state as produced by a suitable electrolytic device, capable of producing separate electrolytically activated, anion-containing and electrolytically activated, cation-containing solutions. The aqueous solution preferably consists of a mixture in a ratio of about 4 to 5 volumes of the electrolytically activated, anion-containing solution to about 1 volume of the electrolytically activated, cation-containing solution.

The anion-containing solution and/or the cation-containing solution may be prepared by means of electrolysis of an aqueous solution of a salt. The salt may be sodium chloride. In particular, it may be non-iodised sodium chloride or potassium chloride.

The anion-containing solution, produced in the anodic chamber of the electrolytic device, is referred to hereinafter as the "anolyte solution" or the "anolyte" and the cation-containing solution, produced in the cathodic chamber of the electrolytic device, is referred to hereinafter as the "catholyte solution" or the "catholyte".

The aqueous solution may be suitable for use also as a cooling, lubricating and irrigating medium in the dental unit and associated dental appliances, thus rendering the solution suitable for use on an at least semi-continuous basis during the treatment of a dental patient.

The dental equipment further may include dispensing means, operatively connected fluidly to the electrolytic device, for dispensing the aqueous solution as an irrigating, cooling, lubricating and disinfecting medium through the dental unit water lines and the dental appliances.

The dispensing means may be suitable for endodontic, orthodontic, periodontal, surgical, pedodontic, restorative and prosthodontic treatment, and is preferably capable of being utilised in any one or more of the treatments selected from the group consisting of drilling, rinsing, ultrasonic descaling and root canal treatment. The dispensing means may have pneumatically, alternatively, hydraulically or electrically driven drilling mechanisms.

The dental unit may be integrated with, alternatively distinct from, the electrolytic device.

The electrolytic device may include an electrolytic cell with predetermined design and geometrical relationships, ensuring optimum fluid flow and recirculation patterns. The cell may have a relatively small, annular, cross-sectional total open area for fluid flow, preferably of about 90 mm$^2$, thus causing turbulent fluid flow there through, so as to ensure maximum exposure of the solutions to the electric field.

The cell may be a through flow, electrolytic cell with two coaxial cylindrical electrodes, with a tubular ceramic diaphragm located coaxially between the two electrodes, so as to separate an annular inter-electrode space into a co-axial, annular catholytic and an annular anolytic chamber arrangement.

The electrolytic cell is preferably suitable to operate under predetermined operational parameters, including a relatively low current of about 1 to 15 A and preferably of about 5 to 7 A, and a relatively high voltage of about 1 to 48 V, preferably of about 6 to 18 V, and more preferably of 12 V, thus providing a relatively high voltage gradient or electric field intensity at the interface between the electrode surface and electrolyte, estimated to be about 10$^6$ V/cm.

According to a second aspect of the invention there is provided an electrolytically activated, anion containing and cation containing aqueous solution for use in the treatment of biofilm in dental unit water lines, the solution being characterised in having microcidal as well as dispersing and surfactant properties capable of eliminating fluid-born and sessile bio-organisms as well as dispersing inert glyco-calyx matrices (hereinafter referred to as "GCM"), thus rendering the solution capable of eliminating biofilm in dental unit water lines.

The aqueous solution may be selected from the group consisting of an anion-containing solution; a cation-containing solution; a mixture of an anion-containing solution and a cation-containing solution; an anion-containing solution, having been prepared from an anion-containing solution, a cation-containing solution or a mixture of an anion-containing solution and a cation-containing solution; and a cation-containing solution, having been prepared from an anion-containing solution, a cation-containing solution or a mixture of an anion-containing solution and a cation-containing solution.

The aqueous solution may consist of a mixture of the electrolytically activated, anion-containing solution and the electrolytically activated, cation-containing solution in any predetermined proportion, such as the proportions required for the production of neutral anolyte, as produced by a suitable electrolytic device, capable of producing separate electrolytically activated, anion-containing and electrolytically activated, cation-containing solutions. The aqueous solution preferably consists of a mixture in a ratio of about 4 to 5 volumes of the electrolytically activated, anion-containing solution to about 1 volume of the electrolytically activated, cation-containing solution.

The anion-containing solution and/or the cation-containing solution may be prepared by means of electrolysis of an aqueous solution of a salt.

The salt may be sodium chloride. In particular, it may be non-iodised sodium chloride or potassium chloride.

The anion-containing solution, produced in the anodic chamber of the electrolytic device, is referred to hereinafter as the "anolyte solution" or the "anolyte" and the cation-containing solution, produced in the cathodic chamber of the electrolytic device, is referred to hereinafter as the "catholyte solution" or the "catholyte".

The neutral to alkaline mixed catholyte and neutral anolyte microcidal solution may be suitable for use also as a cooling, lubricating and irrigating medium in a dental unit and associated dental appliances.

The microcidal solution for use in the dental unit may be produced from an aqueous NaCl solution, the concentration of which may vary between 0.01% to 1% and more specifically between 0.05% and 0.5% and preferably between 0.1% and 0.4%, electrolysed to produce radical cation and radical anion species.

1. The anolyte solution may have a redox potential of about +200 to +1100 mV and more specifically about +600 to +850 mV and preferably equal or more than +713mV and a TDS of about 2–4 g/l. The anolyte solution may have a pH of about 6.75 to 10, preferably about 7.0 to 7.6, and a conductivity of about 0.1 to 10 mS/cm and more specifically of about 0.15 to 4.08 mS/cm, being produced at a current of about 5 Amperes, a voltage of about 12V and a flow rate of about 200 to 500 ml/min and more specifically about 300 to 350 ml/min. The anolyte solution may include species such as $Cl_2$; $HClO$; $HCl$; $HO_2^*$; $HO^*$; $ClO^-$; $H_2O_2$; $^1O_2$; $Cl^*$; $HClO_2$; $ClO_2$; $O^*$; $ClO$; $ClO^-$; $HClO$; $OH^-$; $H_2O_2$; $S_2O_8^{2-}$; $ClO_3^-$; $Cl_2O_6^{2-}$; $HO_2^-$ and $O_3$.

The above radicals in the anolyte solution have been found to have a suitable synergistic anti-microbial effect against viral organisms, spore and cyst-forming bacteria, fungi and yeast. The above anolyte has been found to have a suitable synergistic anti-microbial and/or anti-viral effect which compares favourably with sodium hypochlorite and have been found to be particularly effective against *Prevotella intermedia, Porphyromonas gingivalis, Streptococcus mutans* and *Enterococcus faecalis*.

2. The catholyte solution may have a pH of about 9.0–12.0 and a redox potential of about –864 mV and a conductivity of about 5.92 to 6.03 mS/cm. The catholyte solution may include species such as of $NaOH$; $KOH$; $Ca(OH)_2$; $Mg(OH)_2$; $HO^-$; $H_3O_2$; $HO_2^-$; $H_2O_2^-$; $O_2^{2-}$; $OH^-$; $O_2^{2-}$. $NaOH$; $HO_2^*$; $OH^*$; $H_2O_2$; $H^*$ and $OH^*$.

It is believed that in addition to the normal mechanisms of action involved in elimination of micro-organisms, the oxidising free radicals and other constituents, such as micro-bubbles, present in the anolyte solution act synergistically at a bacterial cellular level, also aiding in the elimination of the micro-organisms in an electrostatic manner.

The efficacy of the mixed anolyte and catholyte solution as an irrigating medium for use in specific procedures, such as in the treatment of cavities and/or root canals, may depend upon the concentration of the mixed anolyte and catholyte solution in the receiving water, as measured by the pH, amperage, oxidation-reduction potential (ORP), conductivity and TDS of the mixed anolyte and catholyte solution, such as the exposure time, such as the contact time between the cavity and/or root canal, and the mixed anolyte and catholyte solution and the temperature during application.

The microcidal solution may be used in its undiluted form, alternatively, may be diluted with potable water for use in the dental unit water lines.

According to a third aspect of the invention there is provided dispensing means, operatively connected fluidly to an electrolytic device, for dispensing an electrolytically activated, neutral to alkaline, anion containing and cation containing aqueous solution, suitable for use in the treatment of biofilm in dental unit water lines, as an irrigating, cooling, lubricating and disinfecting medium through the dental unit water lines and the dental appliances.

The dispensing means may be suitable for endodontic, orthodontic, periodontal, surgical, pedodontic, restorative and prosthodontic treatment, and is preferably capable of being utilised in any one or more of the treatments selected from the group consisting of drilling, rinsing, ultrasonic descaling and root canal treatment. The dispensing means may have pneumatically, hydraulically or electrically driven drilling mechanisms.

According to a fourth aspect of the invention there is provided a method of treating biofilm in DU's, having an arrangement of water lines, the method including the step of generating an electrolytically activated, anion containing and cation containing aqueous solution, characterised in having microcidal as well as dispersing and surfactant properties capable of eliminating fluid-born and sessile bio-organisms as well as dispersing inert glyco-calyx matrices; and introducing such solution at least periodically into the water lines so as to eliminate the biofilm in the water lines.

The method may be characterised in that the solution is introduced also as a cooling, lubricating and irrigating medium in the dental unit and associated dental appliances, thus rendering the solution suitable for use on an at least semi-continuous basis during the treatment of a dental patient.

The method may be characterised in that the solution is introduced continually into the water lines as a cooling, lubricating and irrigating medium as well as to eliminate the biofilm in the water lines.

According to a fifth aspect of the invention there is provided the use of an electrolytically activated, anion containing and cation containing aqueous solution in the treatment of biofilm in dental unit water lines, the solution being characterised in having microcidal as well as dispersing and surfactant properties capable of eliminating fluid-born and sessile bio-organisms as well as dispersing inert glyco-calyx matrices (hereinafter referred to as "GCM"), thus rendering the solution capable of eliminating biofilm in dental unit water lines.

According to a sixth aspect of the invention there is provided a method of dental health care, the method including the step of introducing an electrolytically activated, anion containing and cation containing aqueous solution into dental unit water lines, the solution being characterised in having microcidal as well as dispersing and surfactant properties capable of eliminating fluid-born and sessile bio-organisms as well as dispersing inert glyco-calyx matrices (hereinafter referred to as "GCM"), thus rendering the solution capable of eliminating biofilm in dental unit water lines; and introducing such solution at least periodically into the water lines so as to serve also as a cooling, lubricating and irrigating medium in a dental unit and associated dental appliances, thus rendering the solution suitable for use on an at least semi-continuous basis during the treatment of a dental patient.

A preferred embodiment of the invention will now be described with reference to the accompanying comparative examples.

6. DETAILED DESCRIPTION OF THE INVENTION

The basic electrolytic cells used to generate the electrolytically activated solutions utilised in this specification are substantially as disclosed in U.S. Pat. No 5,635,040. The cells are modular units, and, in various reactor configurations or devices, form the basis of the equipment disclosed in this specification, with the operational specifications for the reactors being optimised for each specific application.

The cell includes a cylindrical metal vessel typically about 210 mm long×16 mm in diameter, having a central rod anode (positive electrode) located within a concentric ceramic tube membrane. The outer tubular wall of the cell reactor acts as the cathode (negative electrode). Provision is made for inlet and outlet ports for the passage of the fluid through it.

Effectively, the ceramic membrane divides the cell into two compartments, the anode compartment and the cathode compartment. Water enters the cell and exits from these compartments as two streams, namely the anolyte and the catholyte, respectively. If so desired, some or all of the catholyte can be returned to the anode compartment so as to vary the properties of the anolyte being produced and vice versa. A number of other hydraulic system possibilities also exist, all of which are designed to achieve specific objectives.

The design of the cell is such as to ensure a very high uniform electric field through which each micro volume of water must pass. In so doing the molecules of water in the anolyte and catholyte acquire special properties which cannot be reproduced by other (more conventional chemical) means. This electrolytic treatment results in the creation of anolyte and catholyte solutions whose pH, oxidation-reduction potentials (ORP) and other physico-chemical properties lie outside of the range which can be achieved by conventional chemical means.

Please note that the pH, oxidation-reduction (Redox) potential (ORP) and concentration values of chlorine, chlorides and other dissolved salts have been determined, unless otherwise stated, as per standard methods of examination of water and effluents.

Please note further that the annotation used for the various electrolytically generated solutions identified in this specification are as found In the Russian literature and patents of Bakhir et al and are as follows:

Anolyte 1.1 A—electrically activated acidic anolyte pH: <5.0

ORP: +800 . . . +1200 mV CSE active species: $Cl_2$, HClO, HCl, $HO^*_2$

This solution results when there is no catholyte feedback and the mineralisation level is high (>5 g/l). Chlorine gas is evolved, the solution is highly oxidizing, corrosive and microcidal. The products are mostly stable.

1.2 AN—electrically activated neutral pH anolyte pH: 5.0–7.0

ORP: +600 . . . +900 mV active species: HClO, $O_3$, $HO^*$, $HO^*_2$

Here some catholyte is re-circulated to the anode compartment and the mineralisation is generally low (<3 g/l). Under these conditions, the formation of highly active but unstable species is favoured. The solution is microcidal but not corrosive, and harmless to human or animal tissue.

1.3 ANK—electrically activated neutral pH anolyte pH: 7.2–8.2

ORP: +250–+800 mV active species: HClO, $ClO^-$, $HO_2^-$, $HO^*_2$, $HO^*$, $H_2O_2$, $^1O_2$, $Cl^-$.

Here a larger flow of catholyte is re-circulated resulting in a higher pH. The solution is still oxidizing and has similar properties to AN, but with a greater degree of short-term activation.

1.4 AND—electrically activated neutral pH anolyte pH: 6.8–7.8

ORP: +700–+1100 mV active species: HClO, $ClO^-$, $HO^-_2$, $HO^*_2$, $H_2O_2$, $^1O_2$, $Cl^*$, $HClO_2$, $ClO_2$, $O_3$, $HO^*$, $O^*$ The solution has a rather high positive ORP and can be used for disinfection.

2.1 K—electrically activated alkaline catholyte pH: >9.0

ORP: −700–−820 mV active species: NaOH, $O^-_2$, $HO^*_2$, $HO_{-2}$, $OH^-$, $OH^*$, $HO_2^-$, $O^{2-}_2$ This solution usually has a pH of 11–12 and is highly reducing. It is very active but the relaxation times are significantly shorter than for anolyte solutions.

2.2 KN—electrically activated neutral catholyte pH: <9.0

ORP: −300–−500 mV active species: $O^-_2$, $HO^*_2$, $HO^-_2$, $H_2O_2$, $H^*$, $OH^*$ When mixed together, in the "as produced" ratios, the anolyte and catholyte form a unique solution, which has both microcidal and anti-oxidant as well as surfactant properties. The dual attributes of this mixture have been shown to be non-toxic for human tissue, as well as having a low corrosion potential profile. The mixture, with its strong oxidation-reduction potential has the capacity to effect the necessary electron transfer between the metastable radical species of the solution and the specific electrical charges present on the biofilm surface, thus destabilising the electrolytic forces at the interface of the GCM and the exposed (non-biofilm coated) conduit surface. This results in the reduced adherence and hence dislodging of the biofilm matrix.

Similarly and when at least a fraction of the catholyte is recycled and channelled back into the anode chamber, the properies of the anolyte, that is subsequently produced, is further modulated. Also similarly, when at least a fraction of the anolyte is recycled and channelled back into the cathode chamber, the properies of the catholyte, that is subsequently produced, is further modulated. Depending on the specifications of the required application, variations in the design of the hydraulic systems can thus be effected so as to produce an activated solution that is mixed and/or generated to meet the requisite objectives.

6. EXAMPLES

Materials and Methods

Organism Used

*Pseudomonas aeruginosa* isolated from a cooling water system was used for all the experiments (10).

Biocide Used

Anolyte and catholyte: In the first experiment anolyte was used in a 1:10 dilution. In the second experiment a combination of anolyte and catholyte at a ratio of 5:1 was used in a 1:10 dilution.

Experimental procedures

A continuous flow—through system Pedersen device (39) was used to determine the biofilm removal of *Ps. aeruginosa* on a stainless steel surface and on glass.

DAPI-staining

DAPI staining was done as described in a previous study (Wolfaardt et al., 1996). Quantification of attached bacteria using 4.6-diamidino-z-phenylidole (DAPI). The 75×27×1 mm coupons, were removed from the Pedersen device and rinsed with sterile water as described for the SEM studies of biofilm formation and stained with DAPI for epifluorescence microscopy (Wolfaardt et al., 1991). Attached bacteria were observed under oil immersion using Epifluorescence microscopy. Ten randomly chosen microscope fields were counted under the 800×magnification.

Scanning Electron Microscopy (SEM)

Coupons (25×27×1 mm) were removed, in duplicate, from the modified Pedersen device at 4, 8, 24, 32, 48 and 56 h, with a sterile forceps and replaced with a sterile coupon, in order to keep the flow constant. After removal the coupons were rinsed with sterile distilled water for 30 s to remove any unattached cells and then fixed for SEM by the following series of treatments: 2% gluteraldehyde (1 h); 0.175M Phosphate-buffer (3×15 min); 50% ethanol (1×15 min); 70% ethanol (1×15 min); 90% ethanol (1×15 min) and 100% ethanol (3×15 min). The coupons were thereafter dried in a critical point dryer, mounted on studs and coated with gold plasma and examined using the Hitachi S-450 scanning electron microscope.

Biofilm Removal

To study biofilm removal, the bacteria were allowed to adhere to the surface of the 3CR12 stainless steel coupons for 168 h in R2A agar, before the dosing of the biocide. The experiment was allowed to proceed for 78 h. Samples were removed before treatment and hourly for 6 h following treatment. Biofilm removal was determined with DAPI and SEM.

Anolyte was added to the system at a 1:10 ratio for the first experiment. A mixture of anolyte/catholyte (5:1) was added at a 1:10 ratio in the second experiment.

For both experiments, a control system, using dam water, where no biocide was added, was included.

Viable Bacteria Counts

The total number of viable bacteria in the planktonic phase was determined before biocide addition and again after 6 h. Plate counts were done on $R_2A$ agar and incubation at ambient temperature to simulate the experimental conditions.

Results and Discussion

Figure 1:
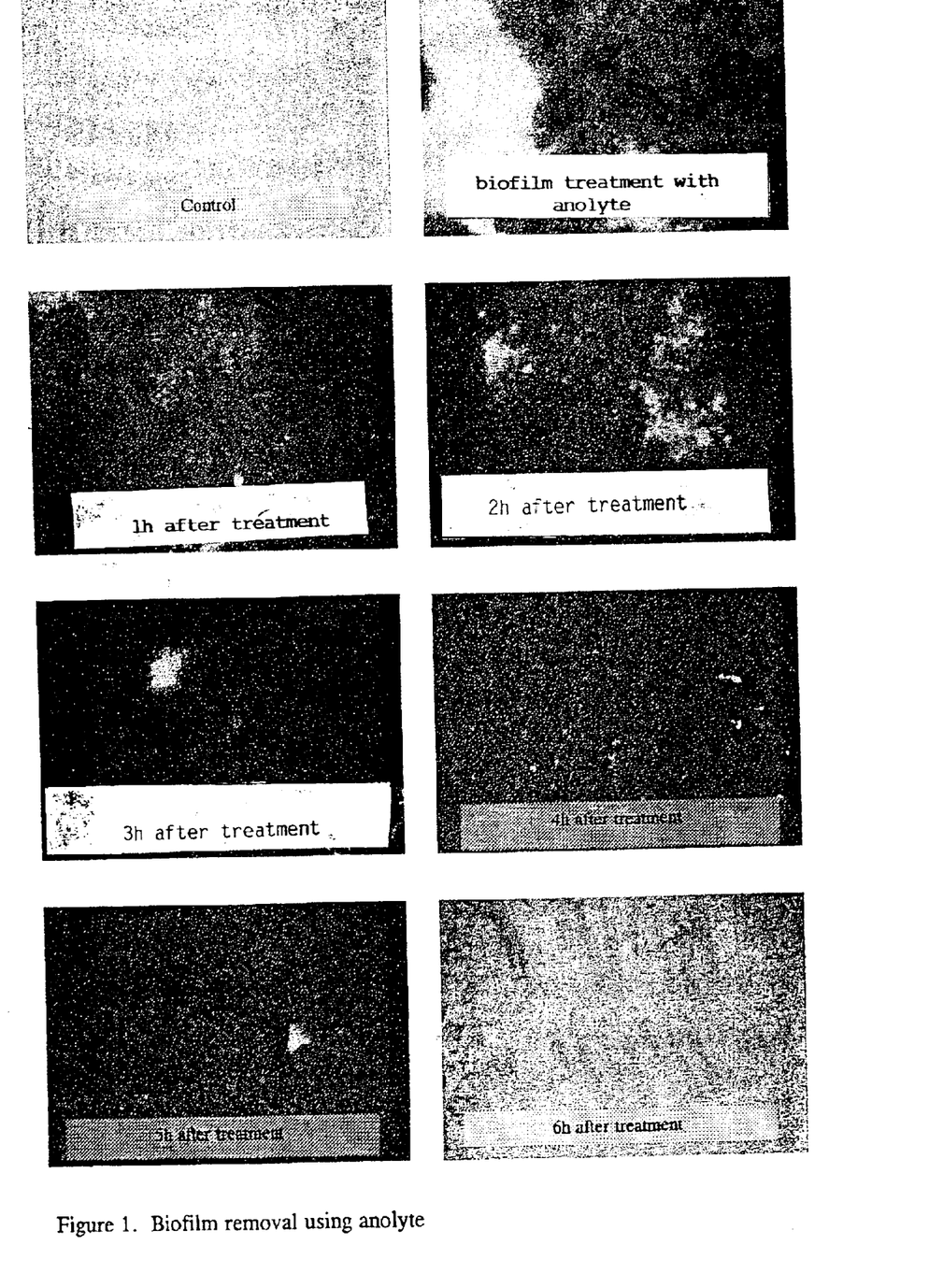
FIG. 1 Illustrates biofilm removal from a stainless steel surface and from glass using anolyte over a period of time.
Figure 2:
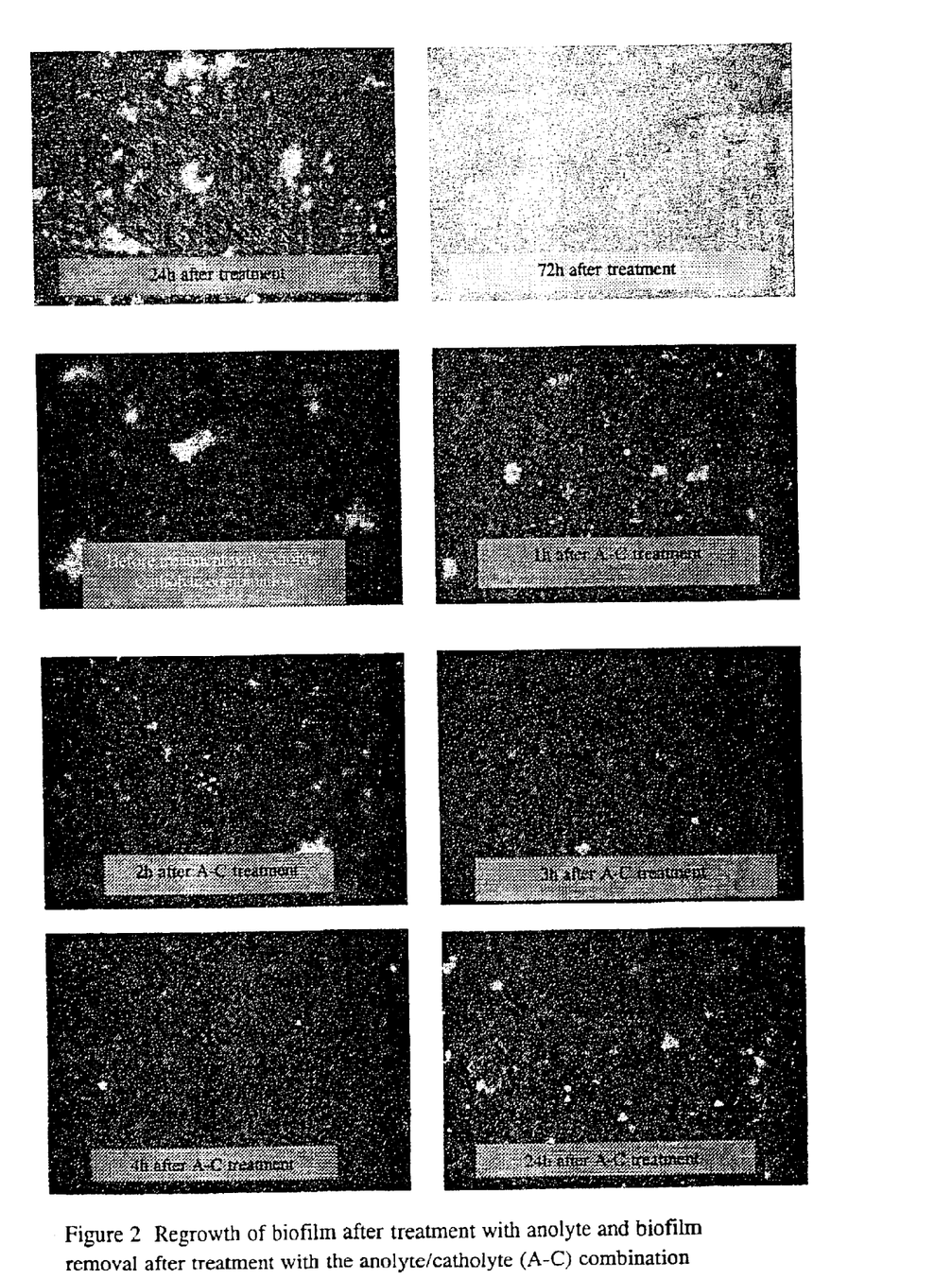
FIG. 2 Illustrates regrowth of biofilm after treatment with anolyte and biofilm removal after treatment with the anolyte/catholyte (A-C) combination.

The anolyte solution (1:10 dilution) effectively removed a mature *P. aeruginosa* biofilm within 6 h (FIG. 1). The anolyte also reduced the planktonic bacteria numbers from $2.41 \times 10^7$ cfu ml$^{-1}$ to <10 cfu ml$^{-1}$ during the same period (Table 1). The anolyte killed the bacteria in the biofilm within 1 h indicated by the fading of the DAPI stain. The system was operated for a further 72 h to determine whether biofilm regrowth would occur. Regrowth of the biofilm was observed 24 h after treatment (FIG. 2). Regrowth of the planktonic bacteria occurred as reflected by the increase in cfu to $1.33 \times 10^6$ cfu ml$^{-1}$ after 72 h (Table 1). These results are in agreement with Brözel and Cloete (10) who indicated that regrowth normally occurs within 48 h after biocide treatment. Regrowth can be attributed to mainly two factors: firstly, in some instances, a microbial population shift may occur to organisms resistant to the biocide, or secondly, the biocide is "consumed" by organic matter allowing the regrowth of the surviving bacteria.

TABLE 1

Planktonic bacterial numbers before and after anolyte treatment

| Time | cfu ml$^{-1}$ |
| --- | --- |
| Before addition | $2.41 \times 1\, 10^7$ |
| After 6 h | <10 |
| After 24 h | <10 |
| After 72 h | $1.33 \times 10^6$ |

Cfu = colony forming units

The anolyte/catholyte (5:1 ratio) solution added at a 1:10 ratio also effectively removed the mature *P. aeruginosa* biofilm. The anolyte/catholyte solution effectively removed the biofilm within 3–4 h (FIG. 2). Noticeable is the dispersion of the biofilm structure (after 1 h) before removal occurs (FIG. 2). Regrowth of the biofilm started taking place 24 h after treatment (FIG. 2). Regrowth of the planktonic bacteria occurred after 72 h (Table 2).

TABLE 2

Planktonic bacterial numbers before and after anolyte/catholyte treatment

| Time | cfu ml$^{-1}$ |
| --- | --- |
| Before addition | |
| After 6 h | $1.14 \times 10^7$ |
| After 24 h | <10 |
| After 72 h | <10 |
| | $1.5 \times 10^6$ |

Cfu = colony forming units

Figure 3:
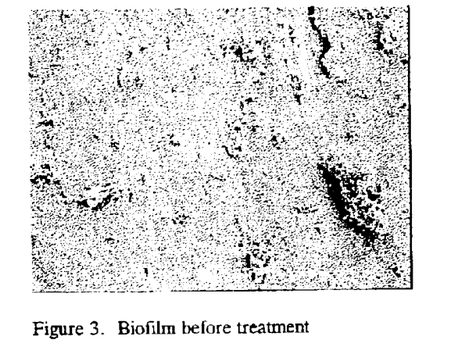
FIG. 3 Illustrates biofilm before treatment.
Figure 4:
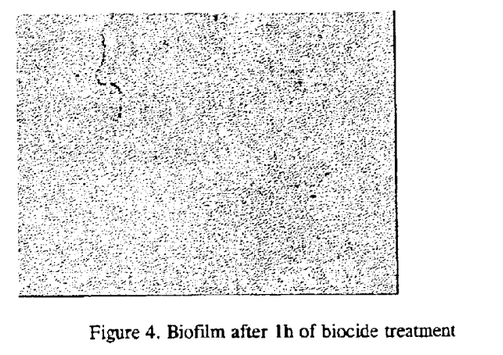
FIG. 4 Illustrates biofilm after 1 hour of biocide treatment.
Figure 5:
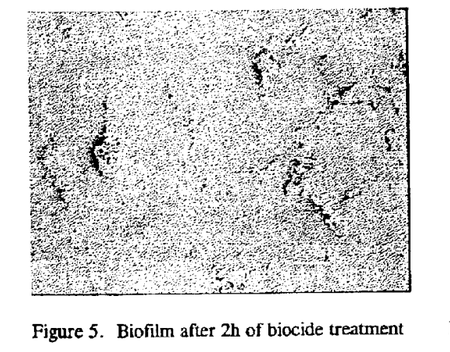
FIG. 5 Illustrates biofilm after 2 hours of biocide treatment.
Figure 6:
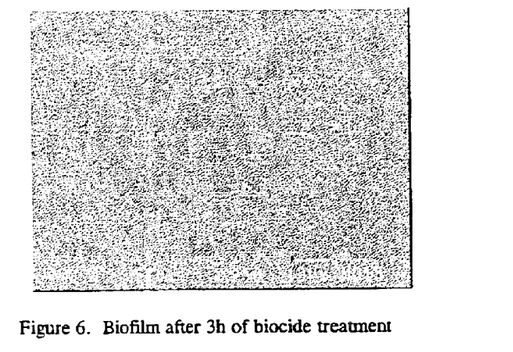
FIG. 6 Illustrates biofilm after 3 hours of biocide treatment.
Figure 7:
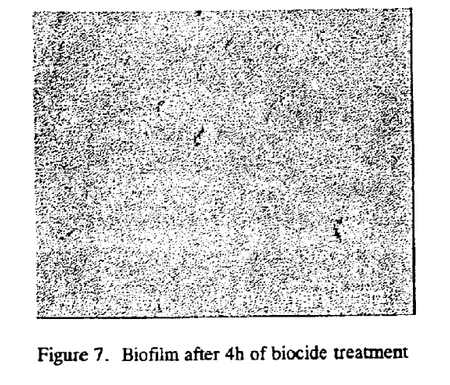
FIG. 7 Illustrates biofilm after 4 hours of biocide treatment.
Figure 8:
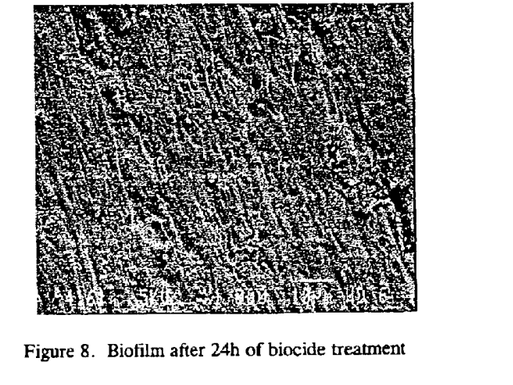
FIG. 8 Illustrates biofilm after 24 hours of biocide treatment.

FIGS. 3–8 are representative scanning electron micrographs of the biofilm behaviour before and after biocide treatment. FIGS. 3 and 4 represent the biofilm before and after 1 h of treatment. Surface colonization can clearly be seen by numerous microcolonies. Also noticeable is the dehydrated glycocalyx structure (biofilm). These microcolonies are still visible after 2 h (FIG. 5) and 3 h (FIG. 6) of treatment. The microcolonies are nevertheless fewer in number and smaller in size than at 0 h and 1 h. After 4 h of treatment (FIG. 7) very few microcolonies were observed and the glycolacyx (biofilm) was no longer noticeable. After 24 h of treatment the situation remained unchanged (FIG. 8).

Nevertheless, DAPI staining indicated regrowth of the biofilm (FIG. 2). This difference was attributed to the difference in the method of preparation for DAPI and SEM, where the preparation of slides for DAPI is less harsh than for SEM.

It will be appreciated that many variations in detail are possible without departing from the scope and/or spirit of the invention as claimed in the claims hereinafter.

What is claimed is:

1. Dental equipment comprising:

an arrangement of dental appliances and associated dental unit water lines;

an electrolytic device arranged in fluid communication with the dental unit water lines for producing an electrolytically activated, microcidal aqueous solution for use in the elimination and control of biofilm in the dental unit water lines, the solution having a pH of between 6.75 and 10 and microcidal, anti-oxidising, dispersing and surfactant properties, the electrolytic device comprising a cylindrical through-flow, electrochemical cell having two co-axial electrodes with a co-axial diaphragm between them so as to separate an annular inter-electrode space into a cathodic and an anodic chamber, such that the electrolytic device enables the harvesting of a separate aqueous predominantly anion-containing solution and a separate aqueous predominantly cation-containing solution, and the application of such solution as two separate product streams, either simultaneously or consecutively, the electrolytic device allowing the mixing of the predominantly anion-containing and the predominantly cation-containing solutions by the separate and independent recirculation of either one or both of the predominantly anion-containing solution and the predominantly cation-containing solution through the same electrode chamber or a counter-electrode chamber so as to modulate the respective properties of the anion- and cation-containing solutions;

and dispensing means fluidly connected to a source of the electrolytically activated, microcidal solution for introducing the aqueous solution into the dental unit water lines for treating the biofilm.

2. The dental equipment as claimed in claim 1, wherein the dispensing means is arranged also for dispensing the microcidal solution as an irrigating, cooling, lubricating and disinfecting medium through the dental appliances during treatment of a dental patient.

3. The dental equipment as claimed in claim 2, wherein the dispensing means is suitable for use in any one or more of the treatments selected from the group consisting of drilling, rinsing, ultrasonic de-scaling and root canal treatment during any one or more of the procedures selected from the group consisting of endodontic, orthodontic, periodontal, surgical, pedodontic, restorative and prosthodontic procedures.

4. The dental equipment as claimed in claim 1, wherein the cell has an annular, cross-sectional total open area of between about 70 to about 110 mm², for fluid flow, causing turbulent fluid flow therethrough so as to ensure maximum exposure of the solution to the electric field, thus effectively disinfecting the dental water to less than 200 colony-forming units per millilitre.

5. An electrolytically activated microcidal aqueous solution for use in the elimination and control of biofilm in dental unit water lines, the solution being characterised in having a pH of between 6.75 and 10 with microcidal as well as anti-oxidising, dispersing and surfactant properties, and further being characterized in that it includes both an aqueous predominantly anion-containing solution and a separate aqueous predominantly cation-containing solution wherein the properties of the respective anion- and cation-containing solutions are modulated by separate and independent recirculation of either one or both of the predominantly anion-containing solution and the predominantly cation-containing solution through the same electrode chamber or a counter-electrode chamber of a cylindrical through-flow, electrochemical cell, rendering the solution bio-compatible and non-corrosive as well as capable of eliminating biofilm in dental unit water lines while simultaneously dispersing and dislodging the biofilm from the water lines so as to reduce the microorganisms to a predetermined level of microorganisms per millilitre in the dental water, the solution further consisting of a mixture of the two activated solutions mixed in a ratio of about 4 to 5 volumes of the electrolytically activated, predominantly anion-containing solution to about 1 volume of the electrolytically activated, predominantly cation-containing solution.

6. The aqueous solution as claimed in claim 5, characterised in being capable of eliminating biofilm in dental unit water lines while simultaneously dispersing and dislodging the biofilm from the water lines so as to reduce the microorganisms to less than 200 colony-forming units of microorganisms per millilitre in the dental water.

7. The aqueous solution as claimed in claim 5, characterised in being selected from the group consisting of a mixture of anion-containing solution and cation-containing solution; an anion-containing solution, having been generated from a cation-containing solution or a mixture of an anion-containing solution and a cation-containing solution; and a cation-containing solution, having been generated from an anion-containing solution, a cation-containing solution or a mixture of an anion-containing solution and a cation-containing solution.

8. The aqueous solution as claimed in claim 5, characterised in having been produced by means of electrolysis of a dilute saline feed solution of about 0.01% to 1%, thus minimising the formation of trihalomethanes and therefore the carcinogenic potential of the solution.

9. The aqueous solution as claimed in claim 5, characterised in being suitable for use also as a cooling, lubricating and irrigating medium in a dental unit and associated dental appliances, thus rendering the solution suitable for use on an at least semi-continuous basis during the treatment of a dental patient.

10. The aqueous solution as claimed in claim 7, characterised in the anion-containing solution having a redox potential of about +200 to +1200 mV, a TDS of about 2–4 g/l a pH of about 6.75 to 10 and a conductivity of about 0.1 to 10 mS/cm mS/cm, produced at a current of about 2 to 15 Amperes, a voltage of about 2 to 48V and a flow rate of about 200 to 500 ml/min.

11. The aqueous solution as claimed in claim 10, characterised in the anion-containing solution having any one or more of species selected from the group consisting of $Cl_2$; $HClO$; $HCl$; $HO_2^*$; $HO^*$; $ClO^-$; $H_2O_2$; $1O_2$; $Cl^*$; $HClO_2$; $ClO_2$; $O^*$; $ClO$; $ClO^-$; $HClO$; $OH^-$; $H_2O_2$; $S_2O_8^{2-}$; $ClO_3^-$; $Cl_2O_6^{2-}$; $HO_2^-$ and $O_3$.

12. The aqueous solution as claimed in claim 7, characterised in the cation-containing solution having a pH of about 9.0–12.0, a redox potential of about −864 mV and a conductivity of about 5.92 to 6.03 mS/cm.

13. The aqueous solution as claimed in claim 12, characterised in the cation-containing solution having any one or more of the species selected from the group consisting of $NaOH$; $KOH$; $Ca(OH)_2$; $Mg(OH)_2$; $HO^-$; $H_3O_2$; $HO_2^-$; $H_2O_2^-$; $O_2^-$; $OH^-$; $O_2^{2-}$. $NaOH$; $HO_2^*$; $OH^*$; $H_2O_2$; $H^*$ and $OH^*$.

14. The aqueous solution as claimed in claim 7, characterised in that activation of the mixed anion and cation containing solution in the receiving dental water, as measured by the pH, oxidation-reduction potential (ORP), conductivity and TDS, the exposure time and the temperature during application is manipulated to optimise the efficacy of the aqueous solution in specific procedures.

15. A method of treating biofilm in dental units having an arrangement of water lines and associated dental appliances, the method including the steps of providing an electrochemical reactor comprising a cylindrical through-flow, electrochemical cell having two co-axial electrodes with a co-axial diaphragm between them so as to separate an annular inter-electrode space into a cathodic and an anodic chamber; introducing a single aqueous feed solution into the electrochemical reactor; electrolytically activating the aqueous solution such that the electrolytically activated aqueous solution includes an aqueous predominantly anion-containing solution and a separate aqueous predominantly cation-containing solution; modulating the respective properties of the predominantly anion-containing solution and the predominantly cation-containing solution by separate and independent recirculation of either one or both of the solutions through the same electrode chamber or a counter-electrode chamber such that the electrolytically activated, microcidal aqueous solution so generated has a pH of between 6.75 and 10 with microcidal as well as anti-oxidising, dispersing and surfactant properties, thus rendering the solution bio-compatible and non-corrosive as well as capable of eliminating biofilm in dental unit water lines while simultaneously dispersing and dislodging the biofilm from the water lines so as to reduce the microorganisms to a predetermined level of microorganisms in the dental water; and introducing the anion-containing solution and the cation-containing solution either simultaneously or consecutively into the water lines so as to eliminate the biofilm in the water lines.

16. The method of treating biofilm as claimed in claim 15, the method being characterised in including the step of introducing the solution also as a cooling, lubricating and irrigating medium in the dental unit and associated dental appliances on an at least semi-continuous basis during the treatment of a dental patient.

17. The method of treating biofilm as claimed in claim 16, the method being characterised in that the microcidal solution is directed through the water lines on a continuous basis during the operation of the dental unit, thus ensuring continuous disinfection of the dental water while providing a cooling, lubricating and irrigating medium through the dental appliances.

18. The method as claimed in claim 15, characterised in that the cell operates under a relatively low current of about 1A to 15A, and a relatively high voltage of about 1V to 48V, so as to provide a relatively high voltage gradient at the interface between the electrode surface and electrolyte of about $10^6$ V/cm as well as a total activated solution at a flow rate, per cell, of between about 35 to 350 ml/min.

19. The use of an electrolytically activated aqueous solution in the treatment of biofilm in dental unit water lines, the solution being characterised in having a pH of between 6.75 and 10 with microcidal as well as anti-oxidising, dispersing and surfactant properties, rendering the solution bio-compatible and non-corrosive as well as capable of eliminating biofilm in dental unit water lines while simultaneously dispersing and dislodging the biofilm from the water lines so as to reduce the micro-organisms to a predetermined level of micro-organisms in the dental water, the solution also being characterized therein that it includes both an aqueous predominantly anion-containing solution and a separate aqueous predominantly cation-containing solution, the solution further being characterised therein its properties are modulated by separate and independent recirculation of either one or both of the predominantly anion-containing solution and the predominantly cation-containing solution through the same electrode chamber or a counter-electrode chamber of cylindrical through-flow, electrochemical cell.

20. A method of dental health care the method including the steps of electrolytically activating an aqueous saline solution such that the electrolytically activated aqueous solution includes both an aqueous predominantly anion-containing solution and a separate aqueous predominantly cation-containing solution; modulating the respective properties of the anion-containing solution and the cation-containing solution by separate and independent recirculation of either one or both of the solutions through the same electrode chamber or a counter-electrode chamber such that the electrolytically activated, microcidal aqueous solution so generated has a pH of between 6.75 and 10 with microcidal as well as anti-oxidising, dispersing and surfactant properties, thus rendering the solution bio-compatible and non-corrosive as well as capable of eliminating biofilm in dental unit water lines while simultaneously dispersing and dislodging the biofilm from the water lines so as to reduce the micro-organisms to a predetermined level of micro-organisms in the dental water; and introducing the electrolytically activated, aqueous anion-containing solution and the cation-containing solution either simultaneously or consecutively into dental unit water lines during the treatment of a dental patient.

* * * * *